US00PP24982P2

(12) United States Plant Patent
Horvath

(10) Patent No.: US PP24,982 P2
(45) Date of Patent: Oct. 21, 2014

(54) ***GEUM* PLANT NAMED 'COSMOPOLITAN'**

(50) Latin Name: ***Geum* hybrid**
Varietal Denomination: Cosmopolitan

(71) Applicant: Brent Horvath, Fontana, WI (US)

(72) Inventor: Brent Horvath, Fontana, WI (US)

( * ) Notice: Subject to any disclaimer, the term of this patent is extended or adjusted under 35 U.S.C. 154(b) by 170 days.

(21) Appl. No.: 13/573,513

(22) Filed: Sep. 20, 2012

(51) Int. Cl.
*A01H 5/00* (2006.01)

(52) U.S. Cl.
USPC ..... Plt./263.1

(58) Field of Classification Search
USPC ..... Plt./263.1
See application file for complete search history.

*Primary Examiner* — Wendy C Haas

(57) ABSTRACT

A new, distinct *Geum* plant as shown and described, characterized by semi double to single flowers of creamy white with red tips.

1 Drawing Sheet

Latin name: *Geum* hybrid.
Cultivar name: 'Cosmopolitan'.

BACKGROUND OF THE INVENTION

The present invention relates to a new and distinct hybrid of *Geum* plant named 'Cosmopolitan' characterized by single to semi double flowers of creamy white and red. The new *Geum* was the result of a breeding program taking place in Hebron, Ill. since 2006. The selection of the new plant was due to its' unique and multi colored semi double to single flowers that have creamy white petals edged in red. Asexual division have been the means of reproduction. The intial division propagation has taken place at a nursery in Hebron, Ill. since 2009. The new *Geum* has shown to be stable and identical in reproduction to the parent after dividing over 60 two year old plants resulting in over 600 divisions from 2009 to 2011.

SUMMARY OF THE INVENTION

In the following description, color references are made to The Royal Horticultural Society Colour Chart (2001). The new *Geum* plant named 'Cosmopolitan' characterized by multi colored semi double to single flowers of creamy white RHS 8D blending into red RHS 51 A to B have been observed to be unique and stable.

Plants of the new *Geum* can be compared to *Geum* 'Tequila Sunrise' U.S. Pat. No. 21,514, patented. 1. The new plant flower colors are RHS 8D blending into red RHS 51 A to B while *Geum* 'Tequila Sunrise' has a bicolor flower of yellow RHG 9B blending into 46A.

It can also be compared to *Geum* 'Mai Tai' U.S. Pat. No. 22,433, patented. 1. The new plant flower colors are RHS 8D blending into red RHS 51 A to B while Geum 'Mai Tai' has a flowers that start red RHS 53B fading to 48C and finally fading to 36B and 36C.

DESCRIPTION OF PHOTOGRAPHS

Figure 1:
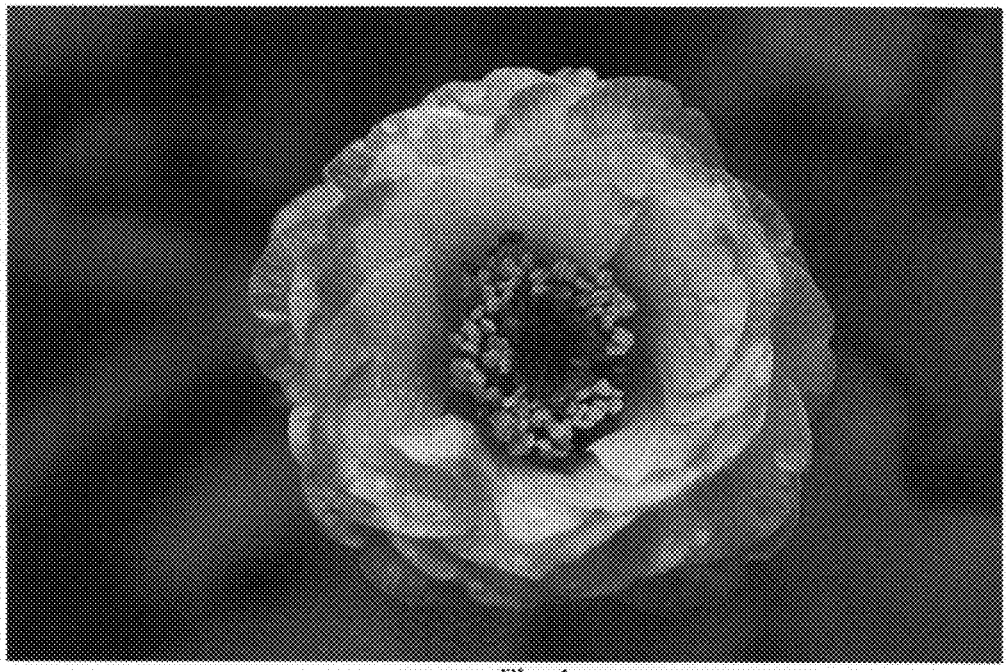
Figure 2:
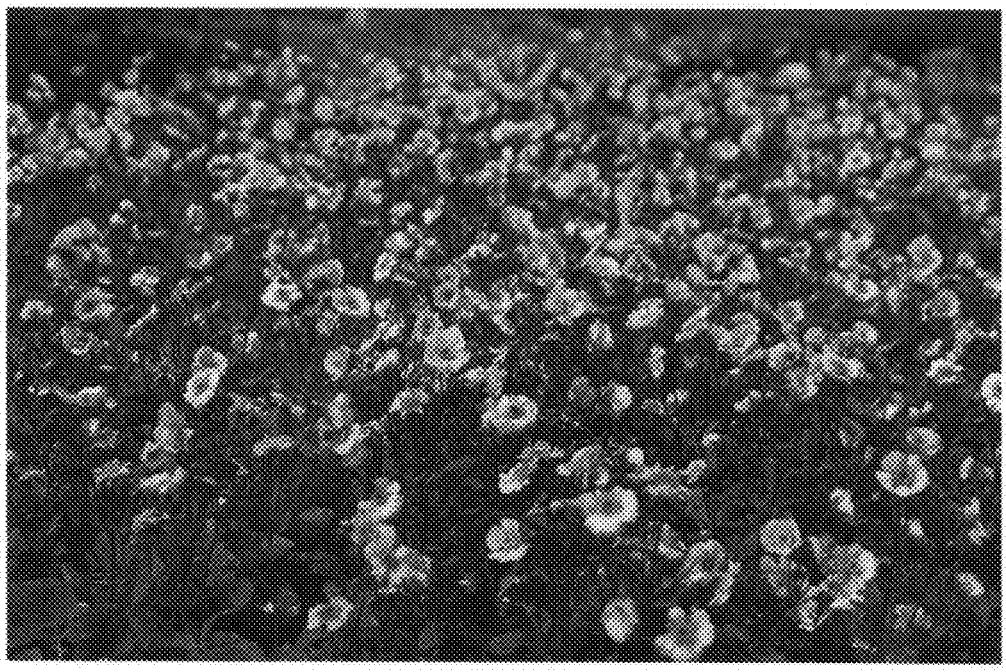

FIG. 1. Close up of the flower.
FIG. 2. Blooming plants in May.

DETAILED BOTANICAL DESCRIPTION

In the following description, color references are made to The Royal Horticultural Society Colour Chart (2001). Plants used for the description were grown in a pot for two years at a nursery in Hebron, Ill. Measurements and numerical values represent averages of typical plants.

Botanical classification: *Geum* hybrid cultivar 'Cosmopolitan'.

Parentage: Unknown.

Propagation: Vegetative division.

Plant description: Overall habit of the new *Geum* is basal clumps, upright burgundy flower stems topped by single and semi double flowers that have flowers with RHS 8D blending into red RHS 51 A to B at the tips of the petals.

*Plant height.*—35 cm.

*Plant width.*—30-35 cm.

*Stem.*—Diameter: 3-4 mm.

*Stem or basal branches.*—Length up to 42 cm, with the internode between basal foliage and first leaflet length being 9-11 cm and the second internode between the first leaflet and the second leaflet length being 6-10 cm and the third internode between the second and third leaflet length being 7-8 cm.

*Stem coloration.*—Of the base of the stem is 145A, coloration of the top of the stem is N77A.

Foliage description:

*Type.*—Deciduous.

*Arrangement.*—Basal alternate with typically two or three lateral leaflets per stem.

*Petiole.*—Up to 7-9 cm long, with a diameter of 5 mm, color N144.

*Terminal compound leaf length.*—Up to 18-20 cm.

*Terminal compound leaf width.*—8 cm.

*Terminal leaflet length.*—Typically 4-5 cm.

*Terminal leaflet width.*—Typically 3-4 cm.

*Terminal leaflet shape.*—Obovate with incised margins.

*Terminal and lateral leaf apex.*—Acute.

*Terminal and lateral leaf base.*—Cuneate.

*Terminal and lateral leaf margin.*—Incised.

*Texture.*—Terminal and lateral leaf, upper and lower surfaces: pubescent.

*Venation pattern.*—Terminal and lateral leaf, upper and lower surfaces: pinnate.

*Venation color.*—Terminal and lateral leaf, upper surface is color 137A and lower surface color is close to 137D.

*Lateral leaflet number.*—2 or 3 per stem.

*Lateral leaflet length.*—1-2 cm.
*Lateral leaflet width.*—Up to 1 cm.
*Lateral leaflet shape.*—Obovate.
*Adaxial leaf description.*—Color is 137A.
*Abaxial leaf description.*—Color is close to 137C.

Flower description:

*Flower type.*—Solitary.
*Flower color.*—8D at the base and 51 A to B at the tips.
*Flower size.*—Diameter: 25-30 mm across, depth 10-15 mm.
*Flower number.*—4-5 per stem, 125 per plant.
*Number flowering stems.*—25.
*Bloom period and duration.*—Beginning May into June in Hebron, Ill.
*Flower longevity and duration on the plant.*—Approximately 3 weeks.
*Flower longevity and duration cut.*—Not measured.
*Scent.*—None.
*Petal count.*—10-20.
*Petal shape.*—Spathulate.
*Petal arrangement.*—Rotate, overlapping.
*Petal diameter or width.*—12 mm across and petal length — 10 mm long.
*Petal apex.*—Retuse, base: attenuate, margin: entire.
*Petal texture.*—upper and lower surfaces: smooth, glabrous.
*Petal color.*—Upper surface is color 8D at the base blending into 51A to B at the tips.
*Petal color.*—Lower surface color is 27C at the base blending into 51B at the tips.
*Inflorescence diameter and height.*—10-11 cm across, 10 cm long.
*Flower buds.*—Diameter: 10-12 mm across, depth: 10 mm, shape: ovoid, surface: slightly pubescent and color 59A.
*Sepal size.*—Length: up to 13 mm, diameter: 6 mm at base coming to a point.
*Sepal quantity.*—6.
*Sepal shape.*—Lanceolate, apex: acute, base: cuneate, margin: entire.
*Sepal texture.*—Upper and lower surfaces: Pubescent.
*Sepal color.*—Adaxial color was not found using the RHS color chart, Abaxial color 59A.
*Peduncle color.*—N 77 A.
*Peduncle size.*—Length: 20-25 mm, diameter: 3 mm.
*Pedicel size.*—Length: 6 cm, diameter: 1-2 mm and color N 77 A.

Reproductive organs: Stamen — quantity: over 100, length: 1 mm, diameter: close to 0.5 mm.

*Anther.*—Quantity: over 100, length: 1 mm, diameter: close to 0.5 mm.
*Pollen.*—Typically present, color: 12 A.
*Stigma.*—None observed.
*Style.*—Number: over 50, length: 6 mm.
*Pistil.*—Number: over 50, length: 6 mm.
*Ovaries.*—None observed.
*Fruit.*—None observed.

Disease resistance: Resistance to diseases common to *Geum* has not been observed on plants grown under nursery conditions.

I claim:

1. A new, distinct *Geum* plant as shown and described, characterized by semi double to single flowers of creamy white with red tips.

* * * * *